United States Patent
Mandeau et al.

(10) Patent No.: US 9,913,874 B2
(45) Date of Patent: Mar. 13, 2018

(54) OBTAINING A JUICE OF FRESH PLANTS BY THERMOMECHANICAL TREATMENT AND COSMETIC AND THERAPEUTIC USE THEREOF

(71) Applicants: PIERRE FABRE DERMO-COSMETIQUE, Boulogne-Billancourt (FR); PIERRE FABRE MEDICAMENT, Boulogne-Billancourt (FR)

(72) Inventors: Anne Mandeau, Toulouse (FR); Christian Talon, Albi (FR)

(73) Assignees: PIERRE FABRE DERMO-COSMETIQUE, Boulogne-Billancourt (FR); PIERRE FABRE MEDICAMENT, Boulogne-Billancourt (FR)

( * ) Notice: Subject to any disclaimer, the term of this patent is extended or adjusted under 35 U.S.C. 154(b) by 0 days.

(21) Appl. No.: 15/022,732

(22) PCT Filed: Sep. 18, 2014

(86) PCT No.: PCT/EP2014/069942
§ 371 (c)(1),
(2) Date: Mar. 17, 2016

(87) PCT Pub. No.: WO2015/040135
PCT Pub. Date: Mar. 26, 2015

(65) Prior Publication Data
US 2016/0243186 A1    Aug. 25, 2016

(30) Foreign Application Priority Data

Sep. 18, 2013  (FR) ...................... 13 58970

(51) Int. Cl.
| | | |
|---|---|---|
| A61K 36/00 | (2006.01) |
| A61K 36/9068 | (2006.01) |
| A23L 2/04 | (2006.01) |
| A61Q 19/00 | (2006.01) |
| A61K 8/97 | (2017.01) |
| A23N 1/02 | (2006.01) |
| A61K 36/9066 | (2006.01) |
| A61K 36/11 | (2006.01) |
| A61K 36/185 | (2006.01) |
| A61K 36/28 | (2006.01) |
| A61K 36/45 | (2006.01) |
| A61K 36/53 | (2006.01) |
| A23P 30/20 | (2016.01) |
| A23L 33/105 | (2016.01) |
| A23L 2/72 | (2006.01) |
| A61K 8/04 | (2006.01) |
| A61K 8/11 | (2006.01) |
| A61K 9/00 | (2006.01) |
| A61K 9/06 | (2006.01) |
| A61K 9/48 | (2006.01) |
| A61K 36/18 | (2006.01) |
| A61K 36/68 | (2006.01) |
| A61K 36/899 | (2006.01) |

(52) U.S. Cl.
CPC ............ *A61K 36/9068* (2013.01); *A23L 2/04* (2013.01); *A23L 2/72* (2013.01); *A23L 33/105* (2016.08); *A23N 1/02* (2013.01); *A23P 30/20* (2016.08); *A61K 8/04* (2013.01); *A61K 8/11* (2013.01); *A61K 8/97* (2013.01); *A61K 9/0014* (2013.01); *A61K 9/0053* (2013.01); *A61K 9/06* (2013.01); *A61K 9/48* (2013.01); *A61K 36/11* (2013.01); *A61K 36/18* (2013.01); *A61K 36/185* (2013.01); *A61K 36/28* (2013.01); *A61K 36/45* (2013.01); *A61K 36/53* (2013.01); *A61K 36/68* (2013.01); *A61K 36/899* (2013.01); *A61K 36/9066* (2013.01); *A61Q 19/00* (2013.01); *A23V 2002/00* (2013.01); *A61K 2236/00* (2013.01); *A61K 2236/31* (2013.01); *A61K 2236/37* (2013.01); *A61K 2800/10* (2013.01)

(58) Field of Classification Search
CPC ....................................... A61K 36/00
USPC ......................................... 424/725
See application file for complete search history.

(56) References Cited

U.S. PATENT DOCUMENTS 5,403,613 A    4/1995 Furui et al.

FOREIGN PATENT DOCUMENTS

| | | |
|---|---|---|
| CA | 2248567 A1 | 9/1997 |
| EP | 0 279 984 A2 | 8/1988 |
| EP | 0 906 113 B1 | 7/2002 |
| SU | 496193 A1 | 12/1975 |
| SU | 1518142 A1 | 10/1989 |

(Continued)

OTHER PUBLICATIONS

Bauer, "Standardization of Echinacea purpurea Expressed Juice with Reference to Cichoric Acid and Alkamides," Journal of Herbs, Spices & Medicinal Plants, 1999, vol. 6, No. 3, pp. 51-62 (13 pages).

(Continued)

*Primary Examiner* — Michael V Meller
(74) *Attorney, Agent, or Firm* — Birch, Stewart, Kolasch & Birch, LLP

(57) ABSTRACT

The present invention relates to a process for obtaining a juice of fresh plants, characterized in that said fresh plants, with the exclusion of the seeds only, are subjected to a thermomechanical treatment consisting in extruding the fresh plants in an extruder, combined with a heat treatment which makes it possible to inactivate the endogenous enzymes and to preserve the molecules of compounds of interest in the native form thereof, in the absence of solvent, followed by a juice recovery operation.

2 Claims, No Drawings

(56) References Cited

FOREIGN PATENT DOCUMENTS

| SU | 1541071 A1 | 2/1990 |
|----|------------|--------|
| SU | 1669978 A1 | 8/1991 |
| WO | WO 97/33596 A1 | 9/1997 |
| WO | WO 2012/098167 A2 | 7/2012 |

OTHER PUBLICATIONS

Bisterfeld Von Meer, "Juice from Cannabis Plants for Food / Beverage, Feed or Biogas," 9th International Conference of the European Industrial Hemp Association, May 23, 2012, pp. 1-15.

Dziezak, "Single and twin-screw extruders in food processing," Food technology, Apr. 1989, pp. 164-174 (12 pages).

International Search Report (Forms PCT/ISA/220 and PCT/ISA/210), dated Dec. 23, 2014, for International Application No. PCT/EP2014/069942.

Khanal et al., "Procyanidin content of grape seed and pomace, and total anthocyanin content of grape pomace as affected by extrusion processing," Journal of Food Science, 2009, vol. 74, No. 6, pp. H174-H182.

Marechal et al., "Characterization of by-products of sunflower culture—commercial applications for stalks and heads," Industrial Crops and Products, 1999, vol. 10, No. 3, pp. 185-200.

Morant et al., "β-Glucosidases as detonators of plant chemical defense," Phytochemistry, 2008 (available online May 9, 2008), vol. 69, No. 9, pp. 1795-1813.

N'Diaye et al., "Extraction of hemicelluloses from poplar, *Populous tremuloides*, using an extruder-type twin-screw reactor: a feasibility study," Bioresource Technology, 1996, vol. 57, pp. 61-67.

N'Diaye et al., "Factors influencing the alkaline extraction of poplar hemicelluloses in a twin-screw reactor: correlation with specific mechanical energy and residence time distribution of the liquid phase," Bioresource Technology, 2000, vol. 75, No. 1, pp. 13-18.

Nüsslein et al., "Enzymatic degradation of Clchoric acid in Echinacea purpurea preparations," J. Nat. Prod., 2000, vol. 63, No. 12, pp. 1615-1618.

Sriti et al., "Oil extraction from coriander fruits by extrusion and comparison with solvent extraction processes," Industrial Crops and Products, 2011 (available online Jan. 26, 2011), vol. 33, pp. 659-664.

White et al., "Polyphenolic composition and antioxidant capacity of extruded cranberry pomace," J. Agric. Food Chem., 2010 (published on web Dec. 18, 2009), vol. 58, No. 7, pp. 4037-4042.

OBTAINING A JUICE OF FRESH PLANTS BY THERMOMECHANICAL TREATMENT AND COSMETIC AND THERAPEUTIC USE THEREOF

The present invention concerns a process for obtaining a juice of fresh plants wherein said fresh plants, with the exclusion of the sole seeds, are subjected to solvent-free thermomechanical treatment followed by a juice recovery operation.

One widely described means to obtain a juice from fresh plants is a pressing process, or grinding and centrifugation.

Patent EP0279984 describes the cosmetic use of juice from a plant in the grass family obtained after extraction by expressing, crushing and/or grinding of the plant.

Aside from fruit juices, medicinal plant juices are also produced (Community herbal monograph EMEA on *Echinacea*, EMEA/HMPC/104945/2006 for example).

The objective of some techniques is to potentiate extraction of membrane constituents, such as the "Flash Release" technique much used for grapes allowing increased extraction of anthocyanins.

The process to obtain a whole fresh plant suspension (SIPF: Suspension intégrale de plantes fraîches) allows fresh plant juice to be obtained in particular using a cryo-crushing step at −25° C. then at −196° C. and macerating the powder obtained in an alcohol solution.

So-called thermomechanical treatment uses mechanical energy under particular, adapted temperature conditions. Examples of mechanical energy inter alia are: pressure, crushing, extrusion, etc.

Extrusion is a process whereby a material able to flow under various controlled conditions is forced to pass through a die at determined speed (Dziezak, J. D. [1989] Single and twin-screw extruders in food processing. Food Technol., April, 164-174). Initially, this technology was used in the metal industry in England at the end of $18^{th}$ century. Sometime later it was introduced into the agrifood industry for the manufacture of sausages and pasta. Today this extrusion technique is used abundantly in the food industry for baking-extrusion of amylaceous products (biscuits, crackers, snacks, etc.), but also for texturizing proteins and the manufacturing of foods for reared and pet animals.

In parallel, extrusion technology has been widely developed for the thermoplastic industry and has led to the design of new screws, further development of the technology and opening up of new applications.

For example several studies have focused on the use of extruders for the conducting of chemical, mechanical, thermomechanical operations in a single continuous step such as for the extraction of hemicelluloses (N'Diaye, S., Rigal, L., Larocque, P., Vidal, P. F., 1996. Extraction of hemicelluloses from poplar populus tremuloides, using an extruder type twin-screw reactor: a feasibility study. Bioresearch Technology 57, 61-67); (N'Diaye S., Rigal L. Factors influencing the alkaline extraction of poplar hemicelluloses in a twin-screw reactor: correlation with specific mechanical energy and residence time distribution of the liquid phase (2000) Bioresource Technology, 75 (1), pp. 13-18), the extraction of pectins (Marechal V., Rigal L. Characterization of by-products of sunflower culture—Commercial applications for stalks and heads (1999) Industrial Crops and Products, 10 (3), pp. 185-200) etc. In these cases an acid or basic solvent is added to the extruder at the same time as the plant raw material to facilitate extraction and solubilisation of the desired macromolecules (reactive extrusion).

Some applications are already known for plant extraction: the use of a single-screw extruder for the expressing of oils from oleaginous seeds without any solvent being injected into the barrel, this oil extraction being based solely on compression of the solid (Sriti J., Talou T., Faye M., Vilarem G. and Marzouk B. Oil extraction from coriander fruits by extrusion and comparison with solvent extraction processes. (2011) Industrial Crops and Products, 33, 659-664).

Extrusion is also used for pre-treatment on fruit pomace (apple, blackcurrant, cranberry . . . ) in association with a solid support such as corn starch to increase extraction of the phenolic compounds (White Brittany L., Howard Luke L., Prior Ronald L. Polyphenolic composition and antioxidant capacity of extruded cranberry pomace. (2010), J. Agric. Food Chem. 58, 4037-4042.) (Khanal R C, Howard L R, Prior R L. Procyanidin content of grape seed and pomace, and total anthocyanin content of grape pomace as affected by extrusion processing. (2009) J Food Sci, 74: H174-82).

Some patents mention obtaining the juice of fresh plants via extrusion and by extrusion is meant a worm screw to convey the plant with piston compressor. The illustrations show a single barrel with a single-screw (SU1669978, SU1541071, SU1518142, SU496193, SU3986103).

Another patent mentions a process to produce juice from fresh plants which, before pressing or filtering, performs pre-treatment either by crushing in an inert atmosphere or bursting via vacuum extrusion. However the extrusion here is not the means to extract juice but to prepare the plant before extraction (EP906113).

Application WO2012/098167 describes the obtaining of cranberry juice and use thereof as beverage, citing cold extrusion as an example of process. The objective here is to maximise preservation of the nutritional qualities of the plant: amino acids, proteins, vitamins. The pressure of the fresh plant to obtain the juice is applied at temperatures between 10 and 40° C. There is no mention therein of thermomechanical treatment.

It is important to recall that when pressing fresh plants, the plant wall sometimes hampers the recovery of some compounds of interest which can therefore be extracted either using an organic solvent or after enzymatic treatment. In addition, the enzymes are easily released and may start to modify the compounds extracted in the juice: hydrolysis, oxidation, deglycosylation, etc.

Surprisingly and unexpectedly the adapting of an extrusion technique widely applied to foods to bake and expand materials for extraction purposes has allowed the recovery of a native extract of a fresh plant. The juice of fresh plants obtained according to the present invention can be given direct cosmetic or therapeutic use.

By "extrusion" according to the present invention is meant thermomechanical treatment whereby the fresh plant is extruded in an extruder, preferably a twin-screw extruder, associated with heat treatment.

In one embodiment, extrusion is characterized by the passing of the fresh plant through a twin-screw extruder composed of:
  a fresh plant feed point: feed hopper;
  the main body of the extruder is formed of one or more barrels in which the worm screws rotate (co-rotating or counter-rotating), or screw segments. Preferably, there are several successive adjacent barrels. Preferably, there are two co-rotating worm screws. The profile of the screws can vary according to the shape of the screw thread (e.g. trapezoidal, conjugate, single or double . . . ) and screw pitch. Each of these screws may also have different segments which may differ from one another by the shape of screw thread and/or pitch. Optionally some of the constituent segments of these screws may also correspond to unilobe or trilobe kneading elements;
  at least one filtering barrel which:
    comes into action when needed for solid/liquid separation;
    further comprises filtering means e.g. a grid, and;
    is particularly located at the extruder outlet;
  heating and cooling means since the barrel must be temperature regulated: 60 to 300° C.

extruder driving means such as:
- a drive unit: composed of a gear motor and torque divider which provide the mechanical power required to rotate the screws;
- automated control means: to monitor and control the process. The parameters able to be adjusted are: screw rotation speed and temperature of each barrel.

In one particular embodiment, the extruder is a twin-screw extruder with co-rotating and co-penetrating screws.

In another particular embodiment of the invention, the process uses an extruder and preferably a twin-screw extruder having several barrels and ending with a filtering barrel, allowing the temperature to be varied and at the same time the applying of shear and intense kneading of the plant raw material, resulting in the entrainment of a large number of compounds, breakdown of the material and also inhibition of endogenous enzymes via heat treatment.

The process of the invention therefore entails extrusion of fresh or frozen plants to extract juice therefrom, recovery and purification (collection) of this juice and finally an optional step to stabilise the collected juice.

The present invention therefore concerns a process to obtain a juice of fresh plants, with only seeds being excluded, subjected to thermomechanical treatment whereby the fresh plants are extruded in an extruder, associated with heat treatment allowing inactivation of endogenous enzymes and preserving of the molecules of compounds of interest in their native form, without use of solvent, followed by a juice recovery operation.

According to one characteristic of the invention, the recovered juice is subjected to a subsequent stabilisation, clarification and/or filtering step.

According to another characteristic of the invention, the thermomechanical treatment consists of shearing trituration at temperatures of between 60° C. and 300° C., preferably between 60° C. and 120° C.

Advantageously the thermomechanical treatment is conducted in a twin-screw extruder having a first co-rotating, co-penetrating twin-screw zone in which trituration of said plants takes place, and a second separate twin-screw zone in which solid/liquid separation takes place. The flow in the twin-screw zone is generated by pumping effect and not by friction forces between screw and barrel as is the case with a single-screw extruder.

According to one characteristic of the invention, said first twin-screw zone is positioned on the fresh plant feed side of the extruder and said second twin-screw zone is positioned on the outlet side of the extruder.

Advantageously each of said zones comprises at least one barrel and preferably several successive adjacent barrels.

According to one additional characteristic of the invention, the different barrels comprise temperature command and control means and heating and/or cooling means.

According to one preferred characteristic of the invention, the twin-screw extruder comprises at least one filtering barrel.

According to another characteristic of the invention, the heating means are formed by a heating collar preferably arranged in the first zone.

Advantageously the feeding, conveying, mechanical shearing and thermomechanical treatment allowing trituration of the fresh plants and juice extraction take place in the first extruder zone, and the liquid/solid separating operation takes place in the second zone.

Advantageously, the first zone comprises several successive barrels the temperatures of which are regulated to obtain increasing temperature levels over a scale of 60° C. to 120° C., and the second zone comprises at least one barrel brought to a temperature of between 30° C. and 120° C., preferably between 30° C. and 100° C.

By "fresh plant" according to the present invention is meant all or part of the plant, with the exclusion of the sole seeds, used fresh or (un)frozen composed of 30 to 80% water, preferably 30-90%.

By "plant part" is meant in particular the above-ground parts such as stalks, branches, leaves, fruit and/or flowers; and/or below-ground parts such as rhizomes, roots and/or bulbs.

In one particular embodiment of the invention, the whole plants are used.

Among the plants which can be used in the present invention the following inter alia can be cited: *Avena sativa, Melilotus officinalis, Tropaeolum majus, Echinaceae* sp., *Urtica dioica, Plantago* sp., *Erigeron canadensis, Equisetum arvense, Calendula officinalis, Melissa officinalis, Physalis* sp., *Vaccinum macrocarpon, Sambucus nigra, Zingiber officinale* et/ou *Curcuma* sp., *Betula* sp., *Mentha* sp., *Althaea* sp., *Poaceae, Asteraceae* and/or *Labieae* and preferably *Avena sativa, Echinaceae purpurea, Urtica dioica, Plantago lanceolate, Equisetum arvense*.

In one particular embodiment the plants are: *Avena sativa* (Oats, above-ground parts), *Melilotus officinalis* (yellow sweet clover, above-ground parts), *Tropaeolum majus* (garden nasturtium, flowering above-ground parts), *Echinaceae* sp. (purple coneflower, flower heads), *Urtica dioica* (nettle, above-ground parts), *Plantago* sp. (plantain, above-ground parts), *Erigeron canadensis* (Canadian horseweed, above-ground parts), *Equisetum arvense* (field horsetail, above-ground parts), *Calendula officinalis* (pot marigold, flowers), *Melissa officinalis* (lemon balm, above-ground parts), *Physalis* sp. (fruits), *Vaccinum macrocarpon* (fruits), *Sambucus nigra* (fruits and/or flowers), *Zingiber officinale* (Ginger, rhizomes) *Betula* sp. (birch, leaves) and/or *Curcuma* sp. (rhizomes).

In one preferred embodiment, the fresh plants are selected from the following group corresponding to plants of which the active constituents are more sensitive to degradation by endogenous enzymes such as polyphenol oxidases, peroxidases, myrosinases, β-glucosidases, lipoxygenase:

*Avena sativa*
*Tropaeolum majus*
*Echinaceae* sp.
*Urtica dioica*
*Plantago* sp.
*Urtica dioica*
*Mentha* sp.
*Melissa officinalis*
*Betula* sp.
*Poaceae*
*Asteraceae*
*Labieae*.

In another particular embodiment of the invention, the plants are oat seedlings.

By "oat seedlings" in the present invention is meant oats before the heading stage i.e. the stage after germination (about 2 weeks to 2 months after germination) during the plant emergence stage up until heading not included. By <<plant emergence>> is meant the growth phase corresponding to stem lengthening and ear formation before flowering. Secondary metabolites are described in application WO2010/054879 as components of an oat seedling extract: flavonoids and saponins of avenacoside type.

According to one embodiment of the present invention, the harvested plants are placed in intermediate storage at 4° C. for transport towards a tunnel freezer at −40° C.

The moisture level of the plants must be at least 30% for full efficacy of the technique.

With this process it is therefore possible to operate using fresh plants which have not undergone any drying step and therefore have maintained their native molecules. Extraction is solvent-free, the process is very fast, the residence time of the plant in the extruder possibly varying from a few seconds to a few minutes and preferably between 10 seconds and 5 minutes, continuously, allowing plant treatment rates to be obtained varying as a function of the size of the extruder of 20 to 500 kg/h corresponding to the obtaining of 10 to 300 l of juice/h.

The mechanical twin-screw extrusion process leads to the formation of a plant plug applying pressure to the material and cell bursting, breakdown of the plant material allowing recovery of a high content of active even scarcely water-soluble components. This brings a major advantage compared with simple pressing or single-screw extrusion.

In addition, the changes in temperature during the extrusion stage allow fluidising of the pomace-plant juice mixture thereby increasing yield if the juice is thick due to the presence of mucilage. This temperature applied throughout the process also allows inactivation of endogenous enzymes and maintaining of the molecules in their native form. This is most important for some compounds which are rapidly inactivated such as glucosinolates for example degraded by myrosinases (crucifers), derivatives of caffeic acids oxidized by polyphenol oxidases (*Echinaceae*) (Nüsslein B., Kurzmann M., Bauer R., Kreis W. Enzymatic degradation of Cichoric acid in *Echinacea purpurea* preparations (2000) J. Nat. Prod., 63, pp. 1615-1618), some phytoalexins activated by deglucosidases (Avenacosides in oats) . . . (Morant A. V., Jorgensen K., Jorgensen C., Paquette S. M., Sanchez-Perez R., Moller B. L., Bak S. β-Glucosidases as detonators of plant chemical defence (2008) Phytochemistry, 69 (9), pp. 1795-1813).

Collecting of the juice whereby the juice of interest is separated from the solid residues can then be obtained by clarifying and/or filtering.

By "clarification" is meant the removal of cell fragments contained in the juice leaving the extruder. This removal can be obtained using clarification technology via centrifugal effect the objective of which is to remove the solid residue which could clog the filtering media. This removal can also be obtained directly by filtering with a filtering aid.

By "filtration" is meant front or cross-flow filtration for which the presence of a filtering aid can be envisaged (perlite, diatom type, etc . . . ). This filtration allows retaining of the last solid residues, the objective being to obtain a perfectly clear solution. It may be followed by membrane filtering with a cut-off threshold defined as a function of the size of the molecules under consideration. It can also be replaced or followed by filtering on resin or silica for enrichment of the compound of interest (e.g. adsorption resins).

In one particular embodiment, the clarification-filtration step is conducted using a filtering barrel integrated at the end of the extruder.

By "stabilisation" according to the present invention is meant:
  to obtain a liquid extract:
    cooling of the juice followed by freezing,
    juice treatment via sterilising 0.22 μm filtration, pasteurisation, U.H.T sterilisation, ultra-filtration and storage in adapted packaging preventing any post-treatment contamination: vacuum-filled sterile pouches, disposable sterile containers.
    storage at ambient temperature at 4° C. or −20° C. (freezing).
    the addition of preserving agents can also be envisaged (e.g. glycols, sorbic, citric acid etc.) or alcohol (minimum 15°).
  to obtain a paste extract: Concentration to obtain a dry matter content of 65% or higher.
  to obtain a dry extract: technologies including vacuum drying, freeze drying or spray drying can be envisaged.

The liquid, paste or dry extracts obtained such as defined above can be used as such in cosmetic, pharmaceutical or food compositions intended to be administered via topical route or oral route.

The chief advantages of the process of the invention compared with existing processes (pressing and single-screw extrusion) are:
  the obtaining of better juice yields in relation to the starting fresh material (juice weight/weight of starting fresh material); and/or
  the obtaining of juice with higher compound content; and/or
  the obtaining of juice containing molecules non-degraded by enzymes released during crushing of the fresh plant.

EXAMPLE 1

12.75 kg of unfrozen (24 h at 2° C.) fresh above-ground parts of oats (*Avena sativa* L.) harvested by harvester after a growth period of 2 months (oat seedlings) were fed into the first barrel of a five-barrel twin-screw extruder with co-rotating, co-penetrating screws—CLEXTRAL BC45. The temperatures applied to the different barrels were 30° C./120° C./120° C./120° C./60° C.

The scheme of the process was as follows (total duration of extrusion step=20 min; treatment rate: 38 kg plants/h and 22 kg juice/h):

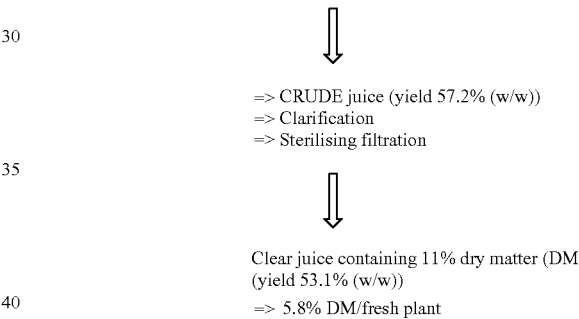

After extrusion, 57.2% juice w/w was obtained relative to the starting material. Clarification and filtration steps were then conducted to obtain a clear juice with a final juice yield of 53.1% containing 11% dry matter i.e. a yield of extracted dry matter of 5.8% (w/w).

The juice yield by pressing (crushing—pressing—filtration) of the same raw material was 50%, containing 4.5% dry matter i.e. a yield of 2.25% (w/w).

The extrusion technology therefore allows more juice to be obtained, the juice having a higher compound content, bioactive compounds in particular. The flavonoid content of the juice obtained in Example 1 was 0.26%, whereas it was only 0.02% in the juice obtained by pressing the same raw material. The flavonoid content was therefore multiplied by 10 in this case.

The advantage of hot extrusion can also be pointed out for flavonoid content: the temperature allows the extraction of more compounds (including four times more flavonoids) and the obtaining of native molecules non-denatured by enzymes.

This was also observed with oat saponins, avenacosides, which are rapidly deglucosylated by pressing. The native molecules are found solely with thermomechanical treatment: the juices obtained by extrusion at 120° C. and 200° C. contained avenacosides (A and B) in a proportion of 89 mg and 93 mg per 100 g of dry matter. They were therefore not degraded by endogenous deglucosidases.

| Technique | Parameters | Juice yield* | DM | Yield DM/fresh plant % | % flavonoids /DM | /juice | /FM | Avenacosides |
|---|---|---|---|---|---|---|---|---|
| Pressing | Crushing then wine press, then filtration | 51 | 3.78 | 1.94 | 0.44 | 0.02 | 0.01 | Degluco avenacosides |
| Extrusion | 25° C. | 59.70 | 7.50 | 4.47 | 0.80 | 0.06 | 0.04 | 0% |
|  | 120° C. | 53.13 | 11 | 5.84 | 2.40 | 0.26 | 0.15 | 89 mg % g DM |
|  | 200° C. | 48.07 | 10 | 4.81 | 2.30 | 0.22 | 0.12 | 93 mg % DM |
| Extraction H2O | 1H reflux |  |  | 3.10 | 1.10 |  | 0.03 |  |

*after filtration

EXAMPLE 2

3.14 kg of unfrozen (18 h at 2° C.) fresh *Echinaceae* flower heads (*Echinacea purpurea* (L.) *Moench*) were fed into the first barrel of the five-barrel twin-screw extruder with co-rotating, co-penetrating screws—CLEXTRAL BC45. The temperatures applied to the different barrels were 100° C./100° C./100° C./100° C./60° C.

The process and mass balance are given in the Table below (total time of extrusion step: 25 min; treatment rate: 7 kg plants/h and 3 kg juice/h):

| MASS BALANCE | PROCESS | DRY MATTER |
|---|---|---|
| 100 | FRESH PLANT |  |
| 48.1 | EXTRUSION | 16.20% |
| 26.9 | CLARIFICATION | 10.81% |
| 25 | FILTRATION | 10.09% |

After extrusion, we therefore obtained 48.1% juice w/w relative to the starting material. Clarification and filtration steps were then performed to obtain a clear juice with final juice yield of 25% containing 10.09% dry matter i.e. a dry matter yield of 2.5% (w/w).

The caffeic acid content of this juice was:
cichoric acid: 1.7%/dry matter i.e. 0.17% w/v
caftaric acid: 1.21% i.e. 0.12% w/v When the juice is extruded at ambient temperature, the content of cichoric and caftaric acid is practically zero due to action of the enzymes. When the juice is obtained by pressing fresh flower heads the content of these molecules is also zero.

The enzymes released when pressing (phenoloxidases) rapidly oxidize these molecules (Nüsslein B., Kurzmann M., Bauer R., Kreis W. Enzymatic degradation of Cichoric acid in *Echinacea purpurea* preparations (2000) J. Nat. Prod., 63, pp. 1615-1618, R. Bauer Standardization of *Echinacea purpurea* Expressed Juice with Reference to Cichoric Acid and Alkamides, Journal of herbs, Spices & Medicinal Plants Vol. 6, Iss. 3, 1999).

When extrusion is conducted at ambient temperature or <60° C., the enzymes are not inactivated and degrade the molecules of interest. In this example, solely extrusions performed at 100° C. or 200° C. allowed extraction from the plant of cichoric and caftaric acids without degradation thereof (see summary Table).

Most of the *Echinaceae* juices available on the market do not contain these molecules, only alcohol-extracted, dried above-ground parts contain these active compounds.

It can also be pointed out that the extrusion process, which as sole solvent uses the water naturally contained in the plant, allows the extraction of far more compounds of interest than aqueous extraction.

| Technique | Parameters | Juice yield | % DM | DM/ fresh plant yield % | Expressed/ dry matter Caftaric acid | Expressed/ dry matter Cichoric acid | Expressed/ fresh plant Caftaric acid mg/g | Expressed/ fresh plant Cichoric acid mg/g |
|---|---|---|---|---|---|---|---|---|
| Pressing | Crushing then wine press | 36 | 7.21 | 2.60 | 0.00 | 0.00 | 0 | 0 |
| Extrusion | 20° C. | 26.7 | 8.41 | 2.24 | 0.06 | 0.04 | 0.014 | 0.009 |
|  | 100° C. | 25.0 | 10.09 | 2.72 | 1.21 | 1.70 | 0.33 | 0.46 |
|  | 200° C. | 12.46 | 12.90 | 1.61 | 1.96 | 3.61 | 0.33 | 0.61 |
| Dried plant extraction | Water under reflux |  |  | 4.73 | 0.22 | 0.05 | 0.1 | 0.023 |

EXAMPLE 3

5.11 kg of unfrozen (20 h at 2° C.) fresh, above-ground parts of Lemon Balm (*Melissa officinalis* L.) were fed into the first barrel of a five-barrel twin-screw extruder with co-rotating and co-penetrating screws—CLEXTRAL BC45. The temperatures applied to the different barrels were 120° C./120° C./120° C./120° C./60° C. The process and mass balance are given in the Table below (duration of extrusion step: 7 min; treatment rate: 46 kg plants/h and 29 kg juice/h):

| MASS BALANCE | PROCESS | DRY MATTER |
|---|---|---|
| 100 | FRESH PLANT |  |
| 62.7 | EXTRUSION |  |

-continued

| MASS BALANCE | PROCESS | DRY MATTER |
|---|---|---|
| 49.2 | CLARIFICATION | |
| 48.8 | FILTRATION | 6.5% |

Under these conditions, extrusion allowed juice to be obtained having a yield close to 50% and containing 6.5% dry matter. This matter inter alia contained rosmarinic acid usually extracted by hydroalcoholic mixtures such as 70% ethanol. The rosmarinic acid content of the dry matter extracted by extrusion without any organic solvent was 2.4% (w/w), i.e. comparable with 70% ethanol extraction.

EXAMPLE 4

4.5 kg of fresh ginger rhizomes (*Zingiber officinale* Roscoe) were fed into the first barrel of a twin-screw extruder with co-rotating and co-penetrating screws—CLEXTRAL BC45. The temperatures applied to the different barrels were 60° C./60° C./60° C./60° C./60° C. The process and mass balance are given in the Table below:

| MASS BALANCE | PROCESS | DRY MATTER |
|---|---|---|
| 100 | FRESH PLANT | |
| 58.9 | EXTRUSION | |
| 50.83 | CLARIFICATION | |
| 50.8 | FILTRATION | 5.2% |

(total time of extrusion step: 5 min; treatment rate: 54 kg plants/h and 32 kg juice/h)

EXAMPLE 5

5.32 kg of fresh curcuma rhizomes (*Curcuma longa* L.) were fed into the first barrel of a twin-screw extruder with co-rotating and co-penetrating screws—CLEXTRAL BC45. The temperatures applied to the different barrels were 120° C./120° C./120° C./120° C./120° C. The process and mass balance are given in the Table below (total time of extrusion step: 10 min; treatment rate: 32 kg plants/h and 13 kg juice/h).

| MASS BALANCE | PROCESS | DRY MATTER |
|---|---|---|
| 100 | FRESH PLANT | |
| 40.6 | EXTRUSION | |
| 34.6 | CLARIFICATION | 7.5% |

The juice obtained was not filtered to preserve the lipophilic compounds in suspension extracted by extrusion: curcumin and derivatives.

Assay showed that the content thereof in the juice obtained was high (8.36%), higher than the content in the dry matter of a commercially available juice (4.52%, containing curcuma juice and citric acid).

| | Technique Parameters | Juice yield | % DM | Curcumin (w/v) % | Curcumin (w/DM) |
|---|---|---|---|---|---|
| marketed juice | Freezing/Unfreezing/DIC*/pressing/stabilisation with citric acid | | 4.01 | 0.181 | 4.52 |
| Extrusion | 120° C. | 34.6 | 7.5 | 0.627 | 8.36 |

*DIC = Detente Instantanee Controlee (Instant controlled pressure drop)

EXAMPLE 6

20.5 kg of unfrozen, fresh above-ground parts of *Plantago lanceolate* (76% humidity) were fed into the first barrel of a five-barrel twin-screw extruder with co-rotating and co-penetrating screws—Clextral BC455. The temperatures applied to the different barrels were 120° C. 43.8% juice was obtained at the outlet of the extruder.

The process and mass balance are given in the Table below:

| PROCESS | MASS BALANCE | DM |
|---|---|---|
| Unfrozen plant | 100 | |
| Extrusion | 45.4 | 8.11% |
| Centrifugation | 42.3 | 7.34% |
| Filtration AF 15 | 41.4 | |
| UF 0.3µ | 38.4 | |
| Filtration AF 140 | 36.6 | 7.11% |
| UF 10 kDa | | 6.20% |

An ultra-filtration step allowed a sap to be obtained of improved organoleptic quality. This sap contained 6.2% dry matter. This dry matter contained the active ingredients of interest: iridoids (1.8%) and phenolic acids (0.3%). These values are close to those obtained with a 30% EtOH hydroalcoholic extract and higher than with an aqueous extract. We therefore obtained a solvent-free extract of equivalent quality to a hydroalcoholic extract.

EXAMPLE 7

18.8 kg of unfrozen, fresh above-ground parts of *Urtica dioica* (76% humidity) were fed into the first barrel of a five-barrel twin-screw extruder with co-rotating and co-penetrating screws—Clextral BC45. The temperature applied to the different barrels was 120° C. 9.4 kg of juice were obtained at the outlet of the extruder, corresponding to a yield of 50%.

This juice, containing 5.7% dry matter after centrifugation, can be used as such after pasteurisation.

| Example 8: capsule | |
|---|---|
| Lemon balm juice as in Example 3, freeze-dried | 200 mg |
| Starch | 45 mg |
| Magnesium stearate | 2 mg |

| Example 9: cream | weight % |
|---|---|
| Oat juice as in Example 1 | 1-5% |
| Tribehenin PEG-20 esters | 2-7% |
| Isodecyl neopentanoate | 2-9% |
| Glycerine | 0.5-10% |
| Glycol palmitate | 1-6% |
| Cetyl alcohol | 0.5-3% |

-continued

| Example 9: cream | weight % |
|---|---|
| Disodium EDTA | 0.05-0.25% |
| Preserving agents | 0.5-3% |
| Flavouring | 0.2-0.5% |
| Xanthan gum | 0.1-0.4% |
| Water | qs |

The invention claimed is:

1. A process to obtain a juice of fresh plants wherein said fresh plants with the exclusion of the sole seeds of the plants are subjected to a solvent-free thermomechanical treatment whereby the fresh plants are extruded in an extruder which is also heated with a heat treatment allowing inactivation of the endogenous enzymes and preserving of the molecules of the compounds of interest in their native form, followed by a juice recovery operation, wherein the thermomechanical treatment is performed in a twin screw extruder which has a first co-rotating and co-penetrating twin screw zone wherein trituration of said plant takes place and wherein the twin screw extruder also has a second twin screw zone wherein solid/liquid separation takes place and wherein said first co-rotating and co-penetrating twin screw zone has several barrels the temperatures of which are regulated to obtain a temperature of 60° C. to 300° C.

2. The process according to claim 1, wherein the temperature is 60° to 120° C.

* * * * *